United States Patent
Sun et al.

(10) Patent No.: US 7,470,681 B2
(45) Date of Patent: *Dec. 30, 2008

(54) PYRIMIDINE COMPOUNDS

(75) Inventors: Lijun Sun, Harvard, MA (US);
Mitsunori Ono, Lexington, MA (US);
Teresa Przewloka, Tewksbury, MA (US); Elena Kostik, Arlington, MA (US); Yumiko Wada, Billerica, MA (US)

(73) Assignee: Synta Pharmaceuticals Corp., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/193,002

(22) Filed: Jul. 29, 2005

(65) Prior Publication Data
US 2006/0030560 A1    Feb. 9, 2006

Related U.S. Application Data

(63) Continuation of application No. 10/655,672, filed on Sep. 5, 2003, now Pat. No. 6,958,332, which is a continuation of application No. 10/192,347, filed on Jul. 10, 2002, now Pat. No. 6,660,733, which is a continuation-in-part of application No. 10/000,742, filed on Nov. 30, 2001, now Pat. No. 6,693,097.

(51) Int. Cl.
| | |
|---|---|
| A61K 31/506 | (2006.01) |
| A61P 17/06 | (2006.01) |
| A61P 19/02 | (2006.01) |
| A61P 25/28 | (2006.01) |
| C07D 401/04 | (2006.01) |
| C07D 405/04 | (2006.01) |
| C07D 413/04 | (2006.01) |
| C07D 417/04 | (2006.01) |
| C07D 239/24 | (2006.01) |

(52) U.S. Cl. .................. 514/227.8; 514/231.5; 514/256; 514/269; 514/275; 544/317; 544/320; 544/336; 544/50; 544/111

(58) Field of Classification Search .............. 514/227.8, 514/231.5, 256, 269, 275
See application file for complete search history.

(56) References Cited

U.S. PATENT DOCUMENTS

| | | | |
|---|---|---|---|
| 6,384,032 B1 | 5/2002 | Ono et al. | |
| 6,660,733 B2 | 12/2003 | Sun et al. | |
| 6,680,315 B2 | 1/2004 | Ono et al. | |
| 6,693,097 B2 | 2/2004 | Ono et al. | |
| 6,706,264 B1 | 3/2004 | Leonard et al. | |
| 6,858,606 B2 | 2/2005 | Sun et al. | |
| 6,958,332 B2 | 10/2005 | Sun et al. | |
| 7,045,517 B2 | 5/2006 | Ono et al. | |
| 7,067,514 B2 | 6/2006 | Ono et al. | |
| 2005/0250787 A1 | 11/2005 | Sun et al. | |
| 2005/0282809 A1 | 12/2005 | Ono et al. | |
| 2006/0025409 A1 | 2/2006 | Ono et al. | |

FOREIGN PATENT DOCUMENTS
WO    WO 00/62778    10/2000

OTHER PUBLICATIONS

European Search Report dated Feb. 7, 2005.
Trincheri, G., "Function and Clinical Use of Interleukin-12", Current Opinion in Hematology, 4: 59-66, 1997.
Mylari, et al., Sorbitol Dehydrogenase Inhibitors (SDIs): A New Potent, Enantiometric SDI, 4- [2-1-R-Hydroxy-ethyl)-pyrimidin-4yl]-piperazine-1-sulfonic Acid Dimethylamide, J. Med. Chem., vol. 44, 2001, pp. 2695-2700.
Arvanitis et al., Non-Peptide Corticotropin-Releasing Hormone Antagonist: Syntheses and Structure-Activity Relationships of 2-Anilinopyrimidines and -triazines, J. Med. Chem., vol. 42, 1999, pp. 805-818.
International Search Report dated Jun. 12, 2003.
Nishigaki et al. "Synthesis of Iminodipyrimidnies", Tetrahedron Letters. 7:539-542 (1969).
Becher, et al., "Experimental Autoimmune Encephalitis and Inflammation in the Absence of Interleukin-12," The Journal of Clinical Investigation, vol. 110, No. 4, pp. 493-497 (2002).
Maeyama, et al., "Attenuation of Bleomycin-induced Pheumopathy in Mice by Monoclonal Antibody to Interleukin-12," Am J Physiol, Lung Cell Mol. Physiol. vol. 280, pp. L1128-L1137 (2001).

*Primary Examiner*—Venkataraman Balasubram
(74) *Attorney, Agent, or Firm*—Edwards Angell Palmer & Dodge LLP; Jeffrey D. Hsi; Mark D. Russett

(57) ABSTRACT

This invention features pyrimidine compounds of formula (I):

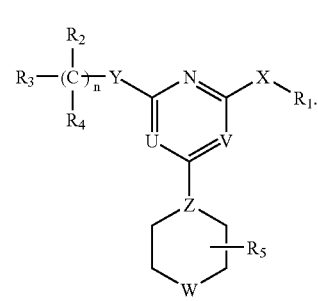

$R_1$ is

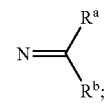

each of $R_2$ and $R_4$ is H; $R_3$ is H, alkyl, aryl, heteroaryl, cyclyl, heterocyclyl, or alkylcarbonyl; $R_5$ is H or alkyl; n is 0, 1, 2, 3, 4, 5, or 6; X is $NR^c$; Y is covalent bond, $CH_2$, C(O), C=N—$R^c$, C=N—$OR^c$, C=N—$SR^c$, O, S, S(O), S(O$_2$), or $NR^c$; Z is N or CH; one of U and V is N, and the other is $CR^c$; and W is O, S, S(O), S(O$_2$), $NR^c$, or NC(O)$R^c$; in which each of $R^a$ and $R^b$, independently, is H, alkyl, aryl, heteroaryl; and $R^c$ is H, alkyl, aryl, heteroaryl, cyclyl, heterocyclyl, or alkylcarbonyl.

25 Claims, No Drawings

PYRIMIDINE COMPOUNDS

RELATED APPLICATIONS

This application is a continuation of U.S. patent application Ser. No. 10/655,672, filed on Sep. 5, 2003, now U.S. Pat. No. 6,958,332, which is a continuation of U.S. patent application Ser No. 10/192,347, filed on Jul. 10, 2002, now U.S. Pat. No. 6,660,733, which is a continuation-in-part of application Ser. No. 10/000,742, filed on Nov. 30, 2001, now U.S. Pat. No. 6,693,097. The contents of each of these patent applications is hereby incorporated by reference.

BACKGROUND

Interleukin-12 (IL-12) is a heterodimeric cytokine (p70) composed of two subunits (p35 and p40), and plays key roles in immune responses by bridging innate resistance and antigen-specific adaptive immunity. Trinchieri (1993) *Immunol Today* 14: 335. For example, it promotes type 1 T helper cell (Th1) responses and, hence, cell-mediated immunity. Chan et al. (1991) *J Exp Med* 173: 869; Seder et al. (1993) *Proc Natl Acad Sci USA* 90: 10188; Manetti et al. (1993) *J Exp Med* 177: 1199; and Hsieh et al. (1993) *Science* 260: 547. Overproduction of IL-12 causes excessive Th1 responses, and may result in inflammatory disorders, such as insulin-dependent diabetes mellitus, multiple sclerosis, rheumatoid arthritis, psoriasis, Crohn's disease, or sepsis. See, for example, Gately et al. (1998) *Annu Rev Immunol.* 16: 495; and Abbas et al. (1996) *Nature* 383: 787. Thus, inhibiting EL-12 overproduction is an approach to treat the just-mentioned diseases. Trembleau et al. (1995) *Immmunol. Today* 16: 383; and Adorini et al. (1997) *Chem. Immunol.* 68: 175. For example, overproduction of IL-12 and the resultant excessive Th1 type responses can be suppressed by modulating IL-12 production. A compound that down-regulates IL-12 production can be used for treating inflammatory diseases. Ma et al. (1998) *Eur Cytokine Netw* 9: 54.

SUMMARY

In one aspect, this invention features pyrimidine compounds of formula (I):

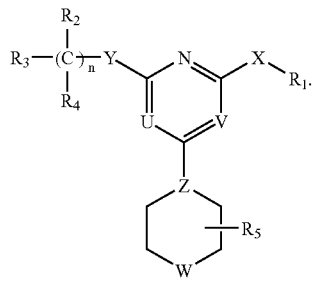

(I)

$R_1$ is

[referred to hereinafter as $NC(R^aR^b)$]; each of $R_2$ and $R_4$ is H; $R_3$ is H, alkyl, aryl, heteroaryl, cyclyl, heterocyclyl, or alkylcarbonyl; $R_5$ is H or alkyl; n is 0, 1, 2, 3, 4, 5, or 6; X is $NR^c$; Y is covalent bond, $CH_2$, $C(O)$, $C=N-R^c$, $C=N-OR^c$, $C=N-SR^c$, O, S, $S(O)$, $S(O_2)$, or $NR^c$; Z is N or CH; one of U and V is N, and the other is $CR^c$; and W is O, S, $S(O)$, $S(O_2)$, $NR^c$, or $NC(O)R^c$; in which each of $R^a$ and $R^b$, independently, is H, alkyl, aryl, heteroaryl; and $R^c$ is H, alkyl, aryl, heteroaryl, cyclyl, heterocyclyl, or alkylcarbonyl. Note that the left atom shown in any substituted group described above is closest to the pyrimidine ring. Also note that when there are more than one $R^c$-containing substituted groups in a pyrimidine compound, the $R^c$ moieties can be the same or different.

In some embodiments, one of $R^a$ and $R^b$ is H or alkyl; and the other is

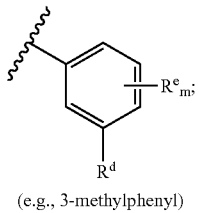

(e.g., 3-methylphenyl)

in which $R^d$ is H, alkyl, or alkoxyl; $R^e$ is halogen, CN, hydroxyl, alkyl, aryl, heteroaryl, alkoxyl, aryloxyl, or heteroaryloxyl; and m is 0, 1, 2, 3, or 4.

In other embodiments, X is NH; Y is O; or n is 2.

In still other embodiments, U is N; V is CH; and $R_3$ is heteroaryl (e.g., 1-oxy-pyridin-2-yl). Preferably, X is NH; Y is O; n is 2; and one of $R^a$ and $R^b$ is H; and the other is 3-methylphenyl.

Alkyl, alkenyl, alkynyl, aryl, heteroaryl (e.g., 1-oxy-pyridinyl), cyclyl, heterocyclyl mentioned above include both substituted and unsubstituted moieties. The term "substituted" refers to one or more substituents (which may be the same or different), each replacing a hydrogen atom. Examples of substituents include, but are not limited to, halogen, hydroxyl, amino, alkylamino, arylamino, dialkylamino, diarylamino, cyano, nitro, mercapto, carbonyl, carbamido, carbamyl, carboxyl, thioureido, thiocyanato, sulfoamido, $C_1$~$C_6$ alkyl, $C_1$~$C_6$ alkenyl, $C_1$~$C_6$ alkoxy, aryl, heteroaryl, cyclyl, heterocyclyl, wherein alkyl, alkenyl, alkoxy, aryl, heteroaryl cyclyl, and heterocyclyl are optionally substituted with $C_1$~$C_6$ alkyl, aryl, heteroaryl, halogen, hydroxyl, amino, mercapto, cyano, or nitro. The term "aryl" refers to a hydrocarbon ring system having at least one aromatic ring. Examples of aryl moieties include, but are not limited to, phenyl, naphthyl, and pyrenyl. The term "heteroaryl" refers to a hydrocarbon ring system having at least one aromatic ring which contains at least one heteroatom such as O, N, or S. Examples of heteroaryl moieties include, but are not limited to, furyl, pyrrolyl, thienyl, oxazolyl, imidazolyl, thiazolyl, pyridinyl, pyrimidinyl, quinazolinyl, and indolyl. The terms "cyclyl" and "heterocyclyl" refer to partially and fully saturated mono- or bi-cyclic rings having from 4 to 14 ring atoms. A heterocyclyl ring contains one or more heteroatoms (e.g., O, N, or S). Exemplary cyclyl and heterocyclyl rings are cyclohexane, piperidine, piperazine, morpholine, thiomorpholine, and 1,4-oxazepane.

Below is an exemplary compound of this invention:

Compound 1:

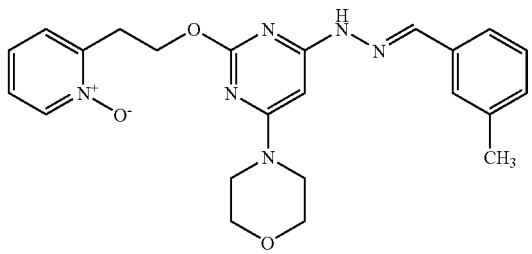

In another aspect, this invention features a pharmaceutical composition that contains a pharmaceutically acceptable carrier and an effective amount of at least one of the pyrimidine compounds of this invention.

In further another aspect, the present invention features a method for treating an IL-12 overproduction-related disorder (e.g., rheumatoid arthritis, sepsis, Crohn's disease, multiple sclerosis, psoriasis, or insulin-dependent diabetes mellitus). The method includes administering to a subject in need thereof an effective amount of one or more pyrimidine compounds of this invention.

The pyrimidine compounds of this invention include the compounds themselves, as well as their salts and their prodrugs, if applicable. Such salts, for example, can be formed between a positively charged substituent (e.g., amino) on a compound and an anion. Suitable anions include, but are not limited to, chloride, bromide, iodide, sulfate, nitrate, phosphate, citrate, methanesulfonate, trifluoroacetate, and acetate. Likewise, a negatively charged substituent (e.g., carboxylate) on a compound can form a salt with a cation. Suitable cations include, but are not limited to, sodium ion, potassium ion, magnesium ion, calcium ion, and an ammonium cation such as teteramethylammonium ion. Examples of prodrugs include esters and other pharmaceutically acceptable derivatives, which, upon administration to a subject, are capable of providing the pyrimidine compounds described above.

In addition, some of the pyrimidine compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms.

Also within the scope of this invention are a composition containing one or more of the compounds described above for use in treating an IL-12 overproduction-related disorder, and the use of such a composition for the manufacture of a medicament for the just-described use.

Other features, objects, and advantages of the invention will be apparent from the description and from the claims.

DETAILED DESCRIPTION

The compounds described above can be prepared by methods well known in the art, as well as by the synthetic routes disclosed herein. For example, a pyrimidine compound can be prepared by using 2,4,6-trichloro-pyrimidine as a starting material. The three chloro groups can be displaced by various substitutes. More specifically, first chloro group (e.g., at position 6) can react with, e.g., morpholine, to form a morpholinyl pyrimidine. 2-Aryl and 2-alkylpyrimidinde dichloro compounds can also be prepared by reacting an amidine with a malonic ester followed by treatment with phosphorous oxychloride. Second chloro group can be replaced by reacting with a nucleophile, such as an alcohol in the presence of base, e.g., sodium hydride. Isomeric forms may be produced. The desired isomeric product can be separated from others by, e.g., high performance liquid chromatography. Third chloro group undergoes a displacement reaction with, e.g., hydrazine, and the primary amine of the coupled hydrazine moiety further reacts with an aldehyde. Thus, a pyrimidine compound of this invention is obtained.

The chemicals used in the above-described synthetic routes may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the pyrimidine compounds. In addition, various synthetic steps may be performed in an alternate sequence or order to give the desired compounds. Synthetic chemistry transformations and protecting group methodologies (protection and deprotection) useful in synthesizing applicable pyrimidine compounds are known in the art and include, for example, those described in R. Larock, *Comprehensive Organic Transformations*, VCH Publishers (1989); T. W. Greene and P. G. M. Wuts, *Protective Groups in Organic Synthesis*, $2^{nd}$ Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

A pyrimidine compound thus obtained can be further purified by flash column chromatography, high performance liquid chromatography, or crystallization.

Also within the scope of this invention is a pharmaceutical composition that contains an effective amount of one or more of the pyrimidine compounds of this invention and a pharmaceutically acceptable carrier. Further, the present invention covers a method of administering an effective amount of such a compound to a subject in need of treatment of IL-12 overproduction related diseases (e.g., rheumatoid arthritis, sepsis, Crohn's disease, multiple sclerosis, psoriasis, or insulin-dependent diabetes mellitus). "An effective amount" refers to the amount of the compound which is required to confer a therapeutic effect on the treated subject. The interrelationship of dosages for animals and humans (based on milligrams per meter squared of body surface) is described in Freireich et al., (1966) *Cancer Chemother Rep* 50: 219. Body surface area may be approximately determined from height and weight of the patient. See, e.g., Scientific Tables, Geigy Pharmaceuticals, Ardley, N.Y., 1970, 537. An effective amount of the pyrimidine compound of this invention can range from about 0.001 mg/Kg to about 1000 mg/Kg. Effective doses will also vary, as recognized by those skilled in the art, depending on the diseases treated, route of administration, excipient usage, and the possibility of co-usage with other therapeutic treatments such as use of other agents.

To practice the method of the present invention, a pyrimidine compound, as a component of a pharmaceutical composition, can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A sterile injectable composition, for example, a sterile injectable aqueous or oleaginous suspension, can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. A pyrimidine compound of this invention can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. For example, solubilizing agents such as cyclodextrins, which form specific, more soluble complexes with the compounds of this invention, or one or more solubilizing agents, can be utilized as pharmaceutical excipients for delivery of the pyrimidine compounds. Examples of other carriers include colloidal silicon dioxide, magnesium stearate, cellulose, sodium lauryl sulfate, and D&C Yellow #10.

The biological activities of a pyrimidine compound can be evaluated by a number of cell-based assays. One of such assays can be conducted using cells from human peripheral blood mononuclear cells (PBMC) or human monocytic cell line (THP-1). The cells are stimulated with a combination of human interferon-γ (IFNγ) and lipopolysaccharide or a combination of IFNγ and *Staphylococcus aureus* Cowan I in the presence of a test compound. The level of inhibition of IL-12 production can be measured by determining the amount of p70by using a sandwich ELISA assay with anti-human IL-12 antibodies. $IC_{50}$ of the test compound can then be determined. Specifically, PBMC or THP-1 cells are incubated with the test compound. Cell viability was assessed using the bioreduction of MTS [3-(4,5-dimethylthiazol-2-yl)-5-(3-carboxymethoxyphenyl)-2-(4-sulfophenyl)-2H-tetrazolium] (Promega, Madison, Wis.).

A pyrimidine compound can also be evaluated by animal studies. For example, one of such studies involves the ability of a test compound to treat adjuvant arthritis (i.e., a IL-12 overproduction related disorder) in rats.

Without further elaboration, it is believed that the above description has adequately enabled the present invention. The following specific embodiments are, therefore, to be construed as merely illustrative, and not limitative of the remainder of the disclosure in any way whatsoever. All of the publications cited herein are hereby incorporated by reference in their entirety.

EXAMPLE 1

Preparation of Compound 1: N-(3-Methyl-benzylidene)-N'-{6-morpholin-4-yl-2-[2-(1-oxy-pyridin-2-yl)-ethoxy]-pyrimidin-4-yl}-hydrazine To a solution of 4-[6-chloro-2-(2-pyridin-2-yl-ethoxy)-pyrimidin-4-yl]-morpholine (1.61 g, 5.0 mmol) in $CH_2Cl_2$ (40 ml) was added methanol (10 ml) followed by the addition of MCPBA (70%, 1.43 g, 5.8 mmol) in one portion. The reaction mixture was stirred overnight at room temperature, affording a clear solution. The solution was cast into saturated aqueous $NaHCO_3$ (35 ml) then the organic phase was separated, washed with 10% aqueous $Na_2S_{2O3}$ (40 ml) and brine (40 ml), and dried ($Na_2SO_4$), filtered and evaporated in vacuo to give a pure product, 4-{6-chloro-2-[2-(1-oxy-pyridin-2-yl)-ethoxy]-pyrimidin-4-yl}-morpholine as a white solid, (1.46 g, 86.7%).

$^1$H-NMR ($CDCl_3$) (ppm), J(Hz): 8.25-8.23 (m, 1H), 7.41-7.7.38 (m, 1H), 7.20-7.16 (m, 2H), 6.14 (s, 1H), 4.71 (t, J=6.0, 2H), 3.77-3.73 (m, 4H), 3.63-3.55 (m, 4H), 3.40 (t, J=6.0, 2H), Anhydrous hydrazine (0.640 ml, 20 mmol) was added to a solution of 4-{6-chloro-2-[2-(1-oxy-pyridin-2-yl)-ethoxy]-pyrimidin-4-yl})-morpholine (1.35 g, 4.0 mmol) in dioxane (15 ml) under the nitrogen protection. The obtained mixture was heated at 95-100° C. for 2 h.

After it was cooled down, the solvent was evaporated in vacuo until the white solid began to precipitate (to a half the original volume), and then $H_2O$ (15 ml) was added. The resulting precipitate was collected by filtration and washed with water (until the pH was neutral). {6-Morpholin-4-yl-2-[2-(1-oxy-pyridin-2-yl)-ethoxy]-pyrimidin-4-yl}-hydrazine (1.02 g) has been obtained in 76.7% yield.

$^1$H-NMR (DMSO-$d_6$) (ppm), J(Hz): 8.25 (bs, 1H), 7.66 (s, 1H), 7.44-7.41 (m, 1H), 7.33-7.25 (m, 2H), 5.59 (s, 1H), 4.46 (t, J=6.0, 2H), 3.64-3.61 (m, 4H), 3.41-3.38 (m, 4), 3.17 (t, J=6, 2H), To a solution {6-morpholin-4-yl-2-[2-(1-oxy-pyridin-2-yl)-ethoxy]-pyrimidin-4-yl}-hydrazine (820 mg, 2.46 mmol) and m-tolualdehyde (97%, 320 mg, 2.58 mmol) in methanol (7 ml) acetic acid (2 drops) was added. The reaction mixture was heated under reflux for 15 min. Upon cooling to room temperature, a precipitating has been formed, and the solid was collected by filtration, washed with little amount of methanol and $Et_2O$, and dried to afford 950 mg (89%) of N-(3-Methyl-benzylidene)-N'-{6-morpholin-4-yl-2-[2-(1-oxy-pyridin-2yl)-ethoxy]-pyrimidin-4-yl}-hydrazine as a white solid (m.p. 187-188° C.). $^1$H NMR (300 MHz, $CDCl_3$), δ (ppm): 10.86 (s, 1H), 8.28-8.26 (m, 1H), 7.98 (s, 1H), 7.50-7.43 (m, 3H), 7.33-7.26 (m, 3H), 7.17 (d, J=7.8 Hz, 1H), 6.05 (s, 1H), 4.53 (t, J=6.3 Hz, 2H), 3.68-3.64 (m, 4H), 3.54-3.50 (m, 4H), 3.21 (t, J=6.3, 2H), 2.33 (s, 3H); ESMS calcd for $C_{23}H_{26}N_6O_3$: 434.21; Found: 457.2 (M+Na)$^+$.

EXAMPLE 2

In Vitro Assays

Reagents. *Staphylococcus aureus* Cowan I (SAC) was obtained from Calbiochem (La Jolla, Calif.), and lipopolysaccharide (LPS, *Serratia marscencens*) was obtained from Sigma (St. Louis, Mo.). Human and mouse recombinant IFN-γ were purchased from Boehringer Mannheim (Mannheim, Germany) and Pharmingen (San Diego, Calif.), respectively.

Human In Vitro Assay. Human PBMC were isolated by centrifugation using Ficoll-Paque (Pharmacia Biotech, Uppsala, Sweden) and prepared in RPMI medium supplemented with 10% fetal calf serum (FCS), 100 U/mL penicillin, and 100 μg/mL streptomycin. PBMC were plated in wells of a 96-well plate at a concentration of $5\times10^5$ cells/well, and primed by adding IFNγ (30 U/mL) for 22 h and stimulated by adding LPS (1 μg/mL), or by adding IFNγ (100 U/mL) and then stimulated by adding SAC (0.01%). A test pyrimidine compound was dissolved in DMSO, and added to wells of the 96-well plate. The final DMSO concentration was adjusted to 0.25% in all cultures, including the compound-free control. Human THP-1 cells were plated in wells, primed by adding IFNγ (100 U/mL) for 22 h and stimulated by adding SAC (0.025%) in the presence of different concentrations of the pyrimidine compound. Cell-free supernatants were taken 18 h later for measurement of cytokines. Cell viability was assessed using the bioreduction of MTS. Cell survival was estimated by determining the ratio of the absorbance in compound-treated groups versus compound-free control.

The supernatant was assayed for the amount of IL-12p40, IL-12p70, or IL-10 by using a sandwich ELISA with anti-human antibodies, i.e., a Human IL-12 p40 ELISA kit from R&D Systems (Berkeley, Calif.), and a Human IL-12 p70 or IL-10 ELISA kit from Endogen (Cambridge, Mass.). Assays were based on the manufacturer's instructions.

Murine In Vitro Assay. Balb/c mice (Taconic, Germantown, N.Y.) were immunized with *Mycobacterium tuberculosis* H37Ra (Difco, Detroit, Mich.). The splenocytes were harvested 5 days and prepared in RPMI medium supplemented with 10% FCS and antibiotics in a flat bottom 96-well plate with $1\times10^6$ cells/well. The splenocytes were then stimulated with a combination of IFNγ (60 ng/mL) and SAC (0.025%) [or LPS (20 μg/mL)] in the presence of a test compound. Cell-free supernatants were taken 24 h later for the measurement of cytokines. The preparation of compound and the assessment of cell viability were carried out as described above. Mouse IL-12 p70, IL-10, IL-1β, and TNFα were measured using ELISA kits from Endogen, according to the manufacturer's instructions.

The biological activities of pyrimidine compounds were tested on human PBMC or THP-1 cells. Unexpectedly, Compound 1 had an $IC_{50}$ value as low as 1.4 nM when tested on human PBMC cells.

EXAMPLE 3

In Vivo Assays

Treatment of adjuvant arthritis in rats: Adjuvant arthritis (AA) was induced in female Lewis rats by the intracutaneous injection (base of the tail) of 0.1 mL of a 10 mg/mL bacterial suspension made from ground, beat-killed *Mycobacterium tuberculosis* H37Ra suspended in incomplete Freund's adjuvant. Rats were given a test compound orally once a day for 12 days, starting the day following the induction. The development of polyarthritis was monitored daily by macroscopic inspection and assignment of an arthritis index to each animal, during the critical period (days 10 to 25 post-immunization).

The intensity of polyarthritis was scored according to the following scheme: (a) Grade each paw from 0 to 3 based on erythema, swelling, and deformity of the joints: 0 for no erythema or swelling; 0.5 if swelling is detectable in at least one joint; 1 for mild swelling and erythema; 2 for swelling and erythema of both tarsus and carpus; and 3 for ankylosis and bony deformity. Maximum score for all 4 paws was thus 12. (b) Grade for other parts of the body: for each ear, 0.5 for redness and another 0.5 if knots are present; 1 for connective tissue swelling (saddle nose); and 1 for the presence of knots or kinks in the tail. The highest possible arthritic index was 16.

Experiments with the AA model were repeated four times. Oral administration of pyrimidine compounds of this invention reproducibly reduced the arthritic score and delayed the development of polyarthritis in a dose-dependent manner. The arthritis score used in this model was a reflection of the inflammatory state of the structures monitored and the results therefore show the ability of the test compound to provide relief for this aspect of the pathology.

Treatment of Crohn's disease in dinitrobenzene sulfonic acid-induced inflammatory bowel syndrome model rats: Wistar derived male or female rats weighing 200±20 g and fasted for 24 hours were used. Distal colitis was induced by intra-colonic instillation of 2,4-dinitrobenzene sulfonic acid (DNBS, 25 mg in 0.5 mL ethanol 30%) after which air (2 mL) was gently injected through the cannula to ensure that the solution remained in the colon. A test compound and/or vehicle was administered orally 24 and 2 hours before DNBS instillation and then daily for 5 days. One control group was similarly treated with vehicle alone while the other is treated with vehicle plus DNBS. The animals were sacrificed 24 hours after the final dose of test compound administration and each colon was removed and weighed. Colon-to-body weight ratio was then calculated for each animal according to the formula: Colon (g)/BW×100. The "Net" increase in ratio of Vehicle-control+DNBS group relative to Vehicle-control group was used as a base for comparison with test substance treated groups and expressed as "% Deduction." A 30% or more reduction in colon-to-body weight ratio, relative to the vehicle treated control group, was considered significant. Unexpectedly, Compound 1 had about 63% reduction.

Rats treated with test substance orally showed a marked reduction in the inflammatory response. These experiments were repeated three times and the effects were reproducible.

Treatment of Crohn's disease in CD4$^+$CD45Rb$^{high}$ T cell-reconstituted SCID colitis model mice: Spleen cells were prepared from normal female BALB/c mice. For cell purification, the following anti-mouse antibodies were used to label non-CD4$^+$T cells: B220 (RA3-6B2), CD11b (M1/70), and CD8α (53-6.72). All antibodies were obtained from BioSource (Camarnllo, Calif.). M450 anti-rat IgG-coated magnetic beads (Dynal, Oslo, Norway) were used to bind the antibodies and negative selection was accomplished using an MPC-1 magnetic concentrator. The enriched CD4$^+$cells were then labeled for cell sorting with FITC-conjugated CD45RB (16A, Pharmingen, San Diego, Calif.) and PE-conjugated CD4 (CT-CD4, Caltag, Burlingame, Calif.). CD4$^+$CD$_{45}^{high}$ cells were operationally defined as the upper 40% of CD45Rb-staining CD4$^+$cells and sorted under sterile conditions by flow cytometry. Harvested cells were resuspended at $4\times10^6$/mL in PBS and injected 100 μL intraperitoneally into female C.B-17 SCID mice. Pyrimidine compounds of this invention and/or vehicle was orally administered once a day, 5 days per week, starting the day following the transfer. The transplanted SCID mice were weighed weekly and their clinical condition was monitored.

Colon tissue samples were fixed in 10% buffered formalin and embedded in paraffin. Sections (4 μm) collected from ascending, transverse, and descending colon were cut and stained with hematoxylin and eosin. The severity of colitis was determined based on histological examination of the distal colon sections, whereby the extent of colonic inflammation was graded on a scale of 0-3 in each of four criteria: crypt elongation, cell infiltration, depletion of goblet cells, and the number of crypt abscesses.

LP lymphocytes were isolated from freshly obtained colonic specimens. After removal of payer's patches, the colon was washed in Ca/Mg-free HBSS, cut into 0.5 cm pieces and incubated twice in HBSS containing EDTA (0.75 mM), DTT (1 mM), and antibiotics (amphotericin 2.5 μg/mL, gentamicin 50 μg/mL from Sigma) at 37° C. for 15 min. Next, the tissue was digested further in RPMI containing 0.5 mg/mL collagenase D, 0.01 mg/mL DNase I (Boehringer Manheim), and antibiotics at 37° C. LP cells were then layered on a 40-100% Percoll gradient (Pharmacia, Uppsala, Sweden), and lymphocyte-enriched populations were isolated from the cells at the 40-100% interface.

To measure cytokine production, 48-well plates were coated with 10 μg/mL murine anti-CD3ε antibody (145-2C11) in carbonate buffer (PH 9.6) overnight at 4° C. $5\times10^5$ LP cells were then cultured in 0.5 ml of complete medium in precoated wells in the presence of 1 μg/mL soluble anti-CD28 antibody (37.51). Purified antibodies were obtained from Pharmingen. Culture supernatants were removed after 48 h and assayed for cytokine production. Murine IFNγ was measured using an ELISA kit from Endogen (Cambridge, Mass.), according to the manufacturer's instructions.

Histological analysis showed that oral administration of pyrimidine compounds of this invention reduced colonic inflammation as compared to vehicle control. The suppressive effect was dose-dependent with a substantial reduction at a dose of 10 mg/kg. The calculated colon-to-body weight ratio was consistent with the histological score, showing attenuation by treatment with the test compound. Furthermore, analysis of cytokines from LP cells in response to anti-CD3 antibody and anti-CD28 antibody demonstrated that LP cells from vehicle control produced an augmented level of IFNγ and treatment with test substance greatly diminished the production. These results clearly demonstrated the potential of the test substance in treatment of inflammatory bowel disease represented by Crohn's disease.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous a pyrimidine compound described in the specification also can be made, screened for their inhibiting IL-12 activities, and used to practice this invention. Thus, other embodiments are also within the claims.

What is claimed is:

1. A method for treating an interleukin-12 overproduction-related disorder selected from rheumatoid arthritis, sepsis, Crohn's disease, multiple sclerosis, psoriasis, or insulin-dependent diabetes mellitus, comprising administering to a subject in need thereof a compound of formula (I):

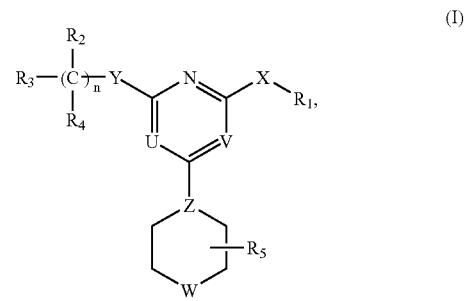

wherein
  $R_1$ is

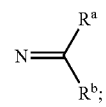

each of $R_2$ and $R_4$ is H;
  $R_3$ is H, alkyl, aryl, heteroaryl, cyclyl, heterocyclyl, or alkylcarbonyl;
  $R_5$ is H or alkyl;
  n is 0, 1, 2, 3, 4, 5, or 6;
  X is $NR^c$;
  Y is covalent bond, $CH_2$, C(O), C=N—$R^c$, C=N—$OR^c$, C=N—$SR^c$, O, S, S(O), S($O_2$), or $NR^c$;
  Z is N or CH;
  one of U and V is N, and the other is $CR^c$; and
  W is O, S, S(O), S($O_2$), $NR^c$, or NC(O)$R^c$;
  in which each of $R^a$ and $R^b$, independently, is H, alkyl, aryl, or heteroaryl; and $R^c$ is H, alkyl, aryl, heteroaryl, cyclyl, heterocyclyl, or alkylcarbonyl; or a pharmaceutically acceptable salt thereof.

2. The method of claim 1, wherein the compound is

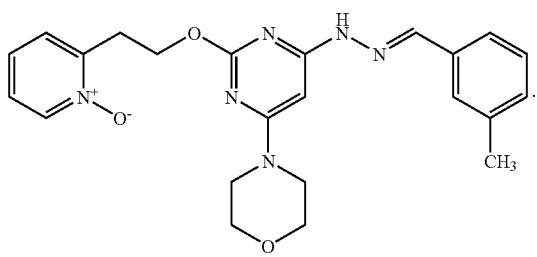

3. The method of claim 1, wherein one of $R^a$ and $R^b$ is H or alkyl; and the other is

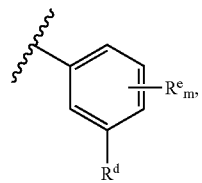

in which $R^d$ is H, alkyl, or alkoxyl; $R^e$ is halogen, CN, hydroxyl, alkyl, aryl, heteroaryl, alkoxyl, aryloxyl, or heteroaryloxyl; and m is 0, 1, 2, 3, or 4.

4. The method of claim 3, wherein one of $R^a$ and $R^b$ is H; and the other is 3-methylphenyl.

5. The method of claim 1, wherein X is NH.

6. The method of claim 5, wherein one of $R^a$ and $R^b$ is H or alkyl; and the other is

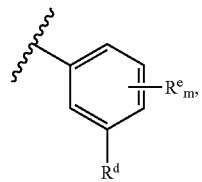

in which $R^d$ is H, alkyl, or alkoxyl; $R^e$ is halogen, CN, hydroxyl, alkyl, aryl, heteroaryl, alkoxyl, aryloxyl, or heteroaryloxyl; and m is 0, 1, 2, 3, or 4.

7. The method of claim 6, wherein one of $R^a$ and $R^b$ is H; and the other is 3-methylphenyl.

8. The method of claim 1, wherein Y is O.

9. The method of claim 8, wherein X is NH.

10. The method of claim 9, wherein one of $R^a$ and $R^b$ is H or alkyl; and the other is

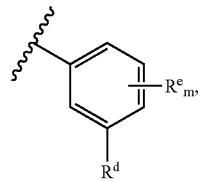

in which $R^d$ is H, alkyl, or alkoxyl; $R^e$ is halogen, CN, hydroxyl, alkyl, aryl, heteroaryl, alkoxyl, aryloxyl, or heteroaryloxyl; and m is 0, 1, 2, 3, or 4.

11. The method of claim 10, wherein one of $R^a$ and $R^b$ is H; and the other is 3-methylphenyl.

12. The method of claim 1, wherein n is 2.

13. The method of claim 12, wherein Y is O.

14. The method of claim 13, wherein X is NH.

15. The method of claim 14, wherein one of $R^a$ and $R^b$ is H or alkyl; and the other is

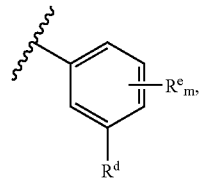

in which $R^d$ is H, alkyl, or alkoxyl; $R^e$ is halogen, CN, hydroxyl, alkyl, aryl, heteroaryl, alkoxyl, aryloxyl, or heteroaryloxyl; and m is 0, 1, 2, 3, or 4.

16. The method of claim 15, wherein one of $R^a$ and $R^b$ is H; and the other is 3-methylphenyl.

17. The method of claim 1, wherein U is N and V is CH.

18. The method of claim 17, wherein Z is N and W is O.

19. The method of claim 18, wherein $R_3$ is heteroaryl.

20. The method of claim 19, wherein $R_3$ is 1-oxy-pyridin-2-yl.

21. The method of claim 20, wherein n is 2.

22. The method of claim 21, wherein Y is O.

23. The method of claim 22, wherein X is NH.

24. The method of claim 23, wherein one of $R^a$ and $R^b$ is H or alkyl; and the other is

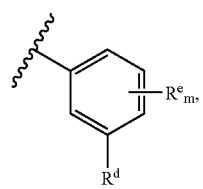

in which $R^d$ is H, alkyl, or alkoxyl; $R^e$ is halogen, CN, hydroxyl, alkyl, aryl, heteroaryl, alkoxyl, aryloxyl, or heteroaryloxyl; and m is 0, 1, 2, 3, or 4.

25. The method of claim 24, wherein one of $R^a$ and $R^b$ is H; and the other is 3-methylphenyl.

* * * * *